United States Patent [19]

Boachie-Adjei et al.

[11] Patent Number: 5,476,463
[45] Date of Patent: Dec. 19, 1995

[54] SPINAL COLUMN RETAINING APPARATUS

[75] Inventors: Oheneba Boachie-Adjei, La Habra, Calif.; Marc A. Asher, Leawood, Kans.

[73] Assignee: AcroMed Corporation, Cleveland, Ohio

[21] Appl. No.: 180,557

[22] Filed: Jan. 12, 1994

[51] Int. Cl.⁶ .................................................. A61B 17/70
[52] U.S. Cl. .............................. 606/61; 403/394
[58] Field of Search .......................... 606/61, 59, 60, 606/73, 72, 53; 403/362, 382, 394

[56] References Cited

U.S. PATENT DOCUMENTS

| | | | |
|---|---|---|---|
| 4,854,311 | 8/1989 | Steffee. | |
| 4,895,141 | 1/1990 | Koeneman et al. | 606/59 |
| 5,024,213 | 6/1991 | Asher et al. | 606/61 |
| 5,127,912 | 7/1992 | Ray et al. | 606/61 |
| 5,129,900 | 7/1992 | Asher et al. | 606/61 |
| 5,312,404 | 5/1994 | Asher et al. | 606/72 |

*Primary Examiner*—Tamara L. Graysay
*Attorney, Agent, or Firm*—Tarolli, Sundheim & Covell

[57] ABSTRACT

An apparatus for retaining vertebrae of a spinal column in a desired spatial relationship includes a fastener having a first end portion for engaging a vertebra. A connector member interconnects the fastener and a longitudinal member positionable along the spinal column. The connector member includes a clamp for clamping the longitudinal member to the connector member. The fastener extends through a slot in the connector member to permit adjustment of the distance between the axis of the fastener and the axis of the longitudinal member. The axis of the fastener is spaced from the clamp a distance measured along the axis of the longitudinal member when the connector member interconnects the fastener and the longitudinal member.

14 Claims, 2 Drawing Sheets

SPINAL COLUMN RETAINING APPARATUS

BACKGROUND OF THE INVENTION

The present invention relates to an apparatus which is used to retain vertebrae of a spinal column in a desired spatial relationship.

A known apparatus for retaining vertebrae in a desired spatial relationship is disclosed in U.S. Pat. No. 5,129,900. The apparatus includes a rod positionable along the spinal column, a fastener for engaging a vertebrae and a connector member for interconnecting the rod and the fastener. The fastener extends through an oblong opening in the connector member to permit relative movement between the rod and the fastener. A set screw clamps the rod to the connector member. The longitudinal axis of the oblong opening extends through the axis of the set screw and perpendicular to the longitudinal axis of the rod. A nut threadably engages the fastener to clamp the connector member to the fastener.

In certain instances, this apparatus interferes with the facet joint of adjacent vertebrae at the ends of the rods. This requires a surgeon to remove all or part of the facet joint of a vertebra that is not being instrumented.

SUMMARY OF THE INVENTION

The present invention provides a new and improved apparatus for retaining vertebrae in a desired spatial relationship. The apparatus includes a fastener having a threaded end portion which engages a vertebra in the spinal column. A connector assembly interconnects the fastener and a longitudinal member, such as a rod, which extends substantially parallel to the axis of the spine. The fastener extends through an oblong opening or a slot in the connector assembly. The distance between the axis of the longitudinal member and the axis of the fastener can be varied while the fastener remains stationary relative to the vertebra to which it is connected.

The longitudinal member is connected to the connector assembly by a clamping member, such as a set screw. The axis of the fastener is spaced from the clamping member a distance measured along the axis of the longitudinal member when the connector assembly interconnects the fastener and the longitudinal member. Thus, the fastener does not interfere with the facet joint of the adjacent vertebrae.

In a first embodiment of the present invention, a longitudinal axis of the oblong opening extends perpendicular to the axis of the longitudinal member. In a second embodiment of the present invention, the longitudinal axis of the oblong opening extends at an acute angle to the axis of the longitudinal member.

BRIEF DESCRIPTION OF THE DRAWINGS

The foregoing and other features of the present invention will become more apparent to one skilled in the art upon reading the following description with reference to the accompanying drawings, wherein.

DESCRIPTION OF THE PREFERRED EMBODIMENTS OF THE INVENTION

Figure 1:
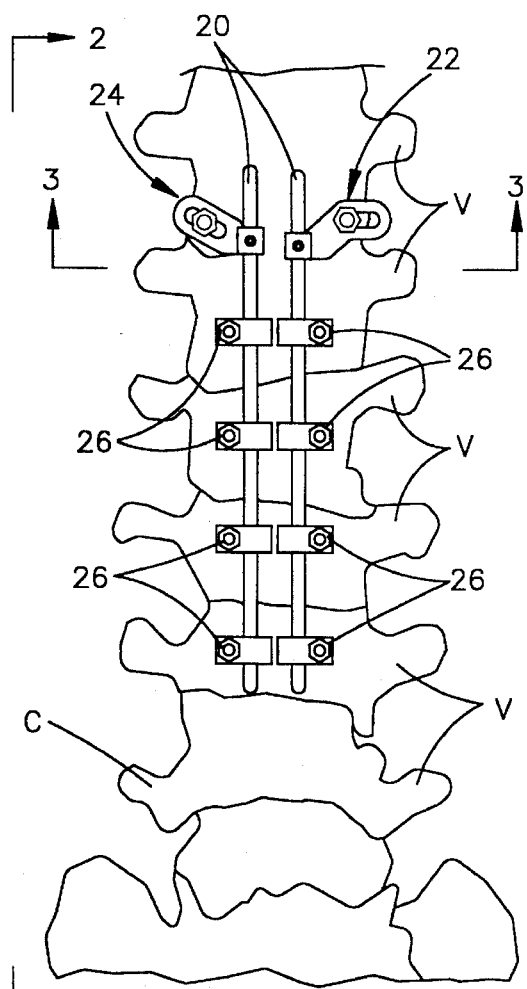
FIG. 1 is a dorsal view of a portion of a spinal column with a retainer assembly constructed in accordance with the present invention to maintain a desired spatial relationship between vertebrae of the spinal column.

A pair of surgically implantable rods 20 (FIGS. 1 and 2) for correcting deformation and/or degeneration of a human spinal column C are connected with several vertebrae V of the spinal column by connector members 22 and 24, which embody the present invention, and connector members 26. The connector members 26 may be any connector members that are well known in the art and may be similar to the connector members of U.S. Pat. No. 5,129,900 which is assigned to the assignee of the present invention.

Figure 2:
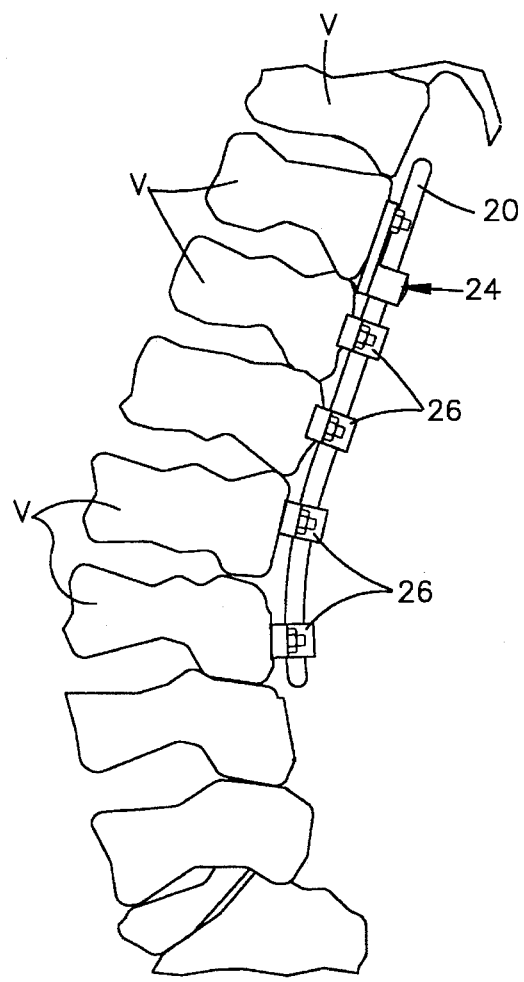
FIG. 2 is a sagittal view of the spinal column of FIG. 1, further illustrating the manner in which the vertebrae of the spinal column are held in the desired spatial relationship.

Each rod 20 is elongate and has a circular cross section taken in a plane extending perpendicular to the longitudinal central axis of the rod. The rod 20 is bendable to any desired plane to conform to a desired curvature of the spinal column C, as illustrated in FIG. 2. The rod 20 has sufficient strength and rigidity to maintain the vertebrae V in the desired relationship.

Figure 3:
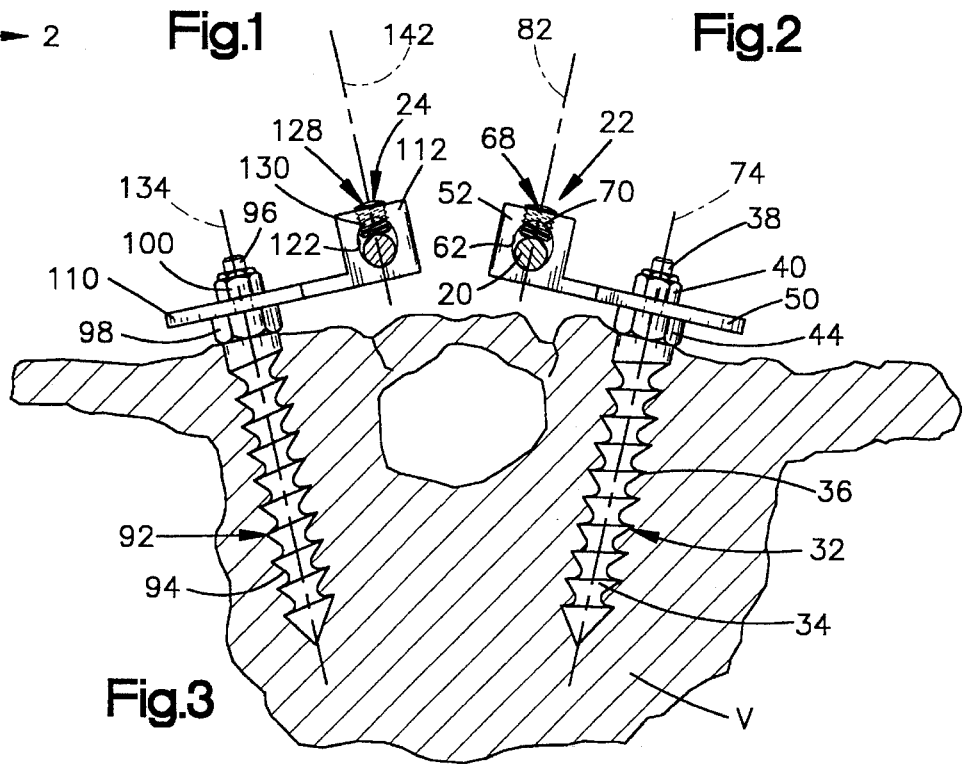
FIG. 3 is a sectional view, taken generally along the line 3—3 of FIG. 1, illustrating the manner in which fasteners are used to connect connector members of the present invention with a vertebra.

In one embodiment of the present invention, the connector member 22 is connected to a respective vertebra V by a fastener 32 (FIG. 3). The fastener 32 has a threaded inner end portion 34 having a coarse helical thread convolution 36 which engages the vertebra V. An outer end portion 38 of the fastener 32 is provided with a relatively fine thread which engages an internal thread convolution on a clamp nut 40. Wrenching flats (not shown) are provided on the outermost end of the outer end portion 38 of the fastener 32. Torque is applied to these wrenching flats to turn the relatively coarse helical thread convolution 36 into the vertebra V. Once the fastener 32 has been connected with the vertebra and the rod 26, the outermost end portion of the fastener is cut away to minimize the overall length of the fastener.

An intermediate portion 44 is provided between the inner end portion 34 and the outer end portion 38 of the fastener 32. The intermediate portion 44 is provided with wrenching flats which can be engaged to hold the fastener 32 against rotation when the clamp nut 40 is tightened. In addition, the intermediate portion 44 of the fastener has a flat outer side surface which abuttingly engages the connector member 22. When the clamp nut 40 is tightened, the connector member 22 is securely gripped between the clamp nut and the intermediate portion 44 of the fastener 32.

Although it is contemplated that the fastener 32 could have many different constructions, it is preferred to construct the fastener 32 in accordance with U.S. Pat. No. 4,854,311 which is assigned to the assignee of the present invention.

The connector member 22 (FIGS. 4 and 5) is made of a suitable biocompatible material, such as stainless steel. The connector member 22 has a mounting section 50 which engages the fastener 32. In addition, the connector member 22 has a rectangular block section 52 which is integrally formed with the mounting section 50 and projects from the mounting section. The block section 52 engages the rod 20.

A slot or an oblong opening 54 extends through the mounting section 50 in a first direction. The outer end portion 38 (FIG. 3) of the fastener 32 extends through the oblong opening 54 and enables the connector member 22 to be moved through a substantial distance relative to the fastener 32. The oblong opening 54 (FIG. 4) has a longitudinal axis 56 that extends perpendicular to the first direction and perpendicular to the longitudinal axis 58 of the rod 20 when the connector member 22 interconnects the fastener 32 and the rod.

The rectangular block section 52 (FIG. 5) of the connector member 22 projects outwardly from the mounting section 50 and receives the rod 20. The block section 52 is provided with an opening 62 through which the rod 20 extends. The opening 62 in the block section 52 could be provided with a generally circular configuration if desired. However, in the embodiment of the present invention, the opening 62 has a generally oval configuration.

Figure 5:
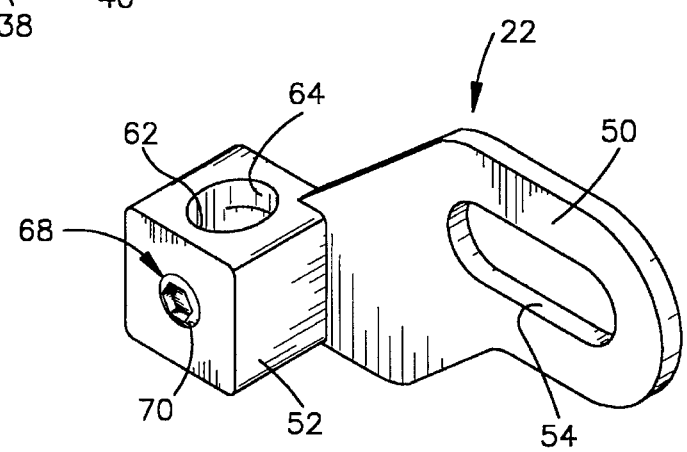
FIG. 5 is a pictorial illustration of the connector member of FIG. 4.

The opening 62 has a pair of axially spaced arcuate surfaces 64, one of which is shown in FIG. 5. The axially spaced arcuate surfaces 64 engage portions of the rod 20 at axially spaced locations. Reference is hereby made to U.S. Pat. No. 5,024,213 to Asher et al. and assigned to the same assignee as the present invention. U.S. Pat. No. 5,024,213 describes the arcuate surfaces and their function in greater detail.

A rod clamp 68 (FIG. 4) holds the rod 20 against movement relative to the connector member 22. The rod clamp 68 includes a set screw 70. The set screw 70 engages an internally threaded opening in the block section 52. The set screw 70 engages the rod 20 to press the rod against the arcuate surfaces 64 in the opening 62.

Figure 4:
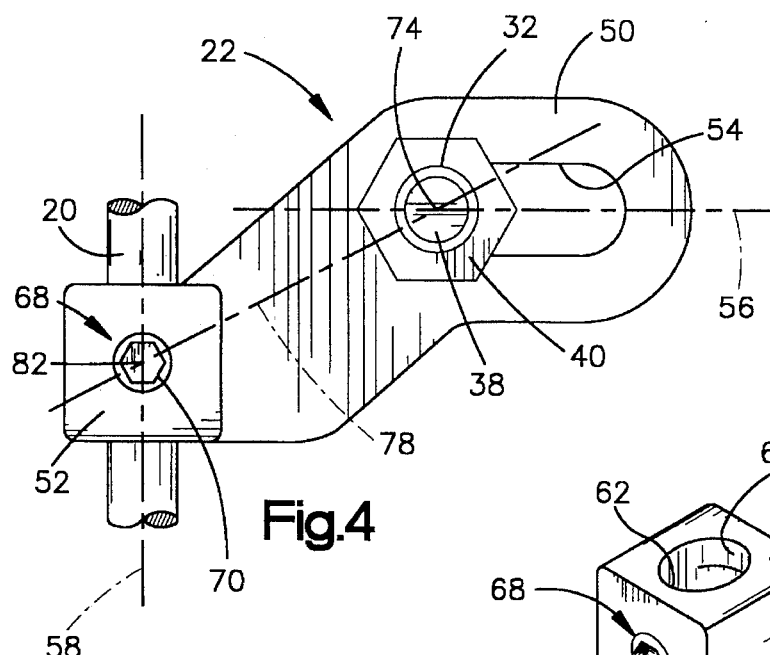
FIG. 4 is an enlarged plan view of a connector member of FIG. 1 illustrating a first embodiment of the present invention.

The longitudinal axis 74 of the fastener 32 is spaced from the rod clamp 68 a distance measured along the longitudinal axis 58 of the rod 20, as seen in FIG. 4. Also, a line 78 extending perpendicular to the axis 74 of the fastener 32 and through the axis 82 of the rod clamp 68 extends at an acute angle to the axis 58 of the rod 20 when the connector member 22 interconnects the rod and the fastener. The oblong opening 54 enables the distance between the axis 74 of fastener 32 and the axis 58 of the rod 20 to be varied. Also, the oblong opening 54 enables the angle between the line 78 and the axis 58 of the rod 20 to be varied.

In another embodiment of the present invention, the connector member 24 is connected to a respective vertebra V by a fastener 92 (FIG. 3). The fastener 92 is identical to the fastener 32 and includes a threaded inner end portion 94, an outer end portion 96 and an intermediate portion 98. The outer end portion 96 of the fastener 92 receives a clamp nut 100. When the clamp nut 100 is tightened, the connector member 24 is securely gripped between the clamp nut and the intermediate portion 98 of the fastener 92.

The connector member 24 is made of a biocompatible material, such as stainless steel. The connector member 24 (FIGS. 6 and 7) has a mounting section 110 which engages the fastener 92. In addition, the connector member 24 has a rectangular block section 112 which is integrally formed with the mounting section 110 and projects from the mounting section. The block section 112 engages the rod 20.

A slot or an oblong opening 114 extends through the mounting section 110 in a first direction. The outer end portion 96 (FIG. 3) of the fastener 92 extends through the oblong opening 114 and enables the connector member 24 to be moved through a substantial distance relative to the fastener 92. The oblong opening 114 (FIG. 6) has a longitudinal axis 116 that extends perpendicular to the first direction and at an acute angle to the longitudinal axis 118 of the rod 20 when the connector member 24 interconnects the fastener 92 and the rod.

Figure 7:
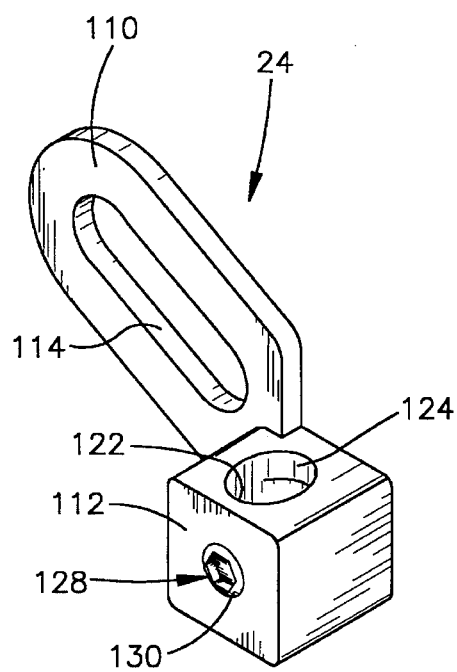
FIG. 7 is a pictorial illustration of the connector member of FIG. 6.

The rectangular block section 112 (FIG. 7) of the connector member 24 projects outwardly from the mounting section 110 and receives the rod 20. The block section 112 is provided with an opening 122 through which the rod 20 extends. The opening 122 in the block section 112 could be provided with a generally circular configuration if desired. However, in the embodiment of the present invention, the opening 122 has a generally oval configuration. The opening 122 has a pair of axially spaced arcuate surfaces 124, one of which is shown in FIG. 7. The axially spaced arcuate surfaces 124 engage portions of the rod 20 at axially spaced locations.

A rod clamp 128 (FIG. 6) holds the rod 20 against movement relative to the connector member 24. The rod clamp 128 includes a set screw 130. The set screw 130 engages an internally threaded opening in the block section 112. The set screw 130 engages the rod 20 to press the rod against the arcuate surfaces 124 in the opening 122.

Figure 6:
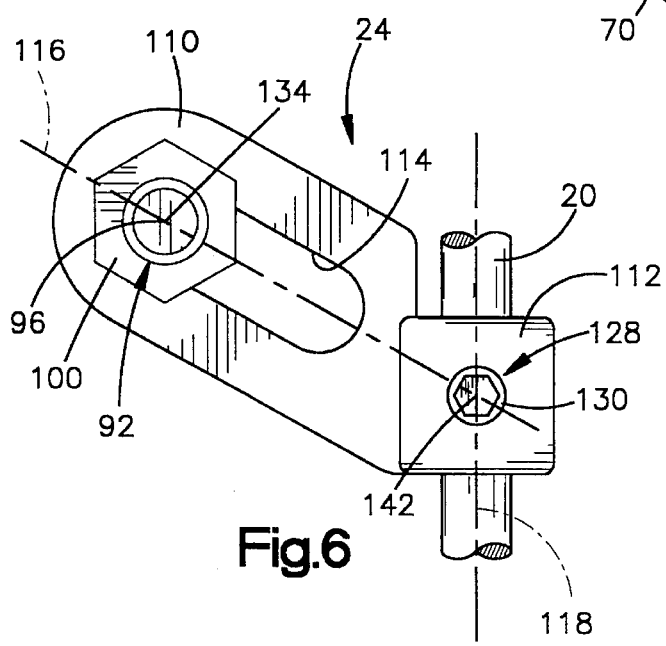
FIG. 6 is an enlarged plan view of a connector member of FIG. 1 illustrating a second embodiment of the present invention.

The longitudinal axis 134 of the fastener 92 is spaced from the rod clamp 128 a distance measured along the longitudinal axis 118 of the rod 20, as seen in FIG. 6. The longitudinal axis 116 of the oblong opening 114 extends perpendicular to the axis 134 of the fastener 92 and through the axis 142 of the rod clamp 128 and at an acute angle to the axis 118 of the rod 20 when the connector member 24 interconnects the rod and the fastener. The oblong opening 114 enables the distance between the axis 134 of the fastener 92 and the axis 118 of the rod 20 to be varied. Also, the oblong opening 114 enables the distance between the fastener 92 and the rod clamp 128 to be varied. From the above description of the invention, those skilled in the art will perceive improvements, changes and modifications. Such improvements, changes and modifications within the skill of the art are intended to be covered by the appended claims.

Having described the invention, the following is claimed:

1. An apparatus for retaining vertebrae of a spinal column in a desired spatial relationship comprising:

a fastener having a first end portion for engaging a vertebra and a second end portion;

a longitudinal member positionable along the spinal column; and a one piece connector means for interconnecting said fastener and said longitudinal member, said connector means including clamping means for clamping said longitudinal member to said connector means, and a slot through which said second end portion of said fastener is extendable, said slot enabling adjustment of the distance between the axis of said fastener and the axis of said longitudinal member, said slot having a longitudinal axis extending at an acute angle to the axis of said longitudinal member when said connector means interconnects said fastener and said longitudinal member, the axis of said fastener being spaced from said clamping means a distance measured along the axis of said longitudinal member when said connector means interconnects said fastener and said longitudinal member.

2. An apparatus as set forth in claim 1 wherein said fastener includes an intermediate portion located between said first and second end portions; said intermediate portion being engageable with said connector means to position said connector means axially along said fastener.

3. An apparatus as set forth in claim 2 further including a nut threadably engageable with said second end portion of said fastener; said nut and said intermediate portion of said fastener gripping said connector means to connect said connector means to said fastener.

4. An apparatus as set forth in claim 1 wherein said connector means includes a mounting section engageable with said fastener and a block section engageable with said longitudinal member.

5. An apparatus as set forth in claim 4 wherein said block section includes an opening through which said longitudinal member is extendable.

6. An apparatus for retaining vertebrae of a spinal column in a desired spatial relationship comprising:

a fastener having a first end portion for engaging a vertebra and a second end portion;

a longitudinal member positionable along the spinal column; and a one piece connector means for interconnecting said fastener and said longitudinal member, said connector means including clamping means for clamping said longitudinal member to said connector means, and a slot through which said second end portion of said fastener is extendable, said slot having a longitudinal axis extending through a longitudinal axis of said clamping means, said slot enabling adjustment of the distance between the axis of said fastener and the axis of said longitudinal member, the axis of said fastener being spaced from said clamping means a distance measured along the axis of said longitudinal member when said connector means interconnects said fastener and said longitudinal member.

7. An apparatus as set forth in claim 6 wherein said clamping means includes a set screw engageable with said longitudinal member.

8. An apparatus for retaining vertebrae of a spinal column in a desired spatial relationship comprising:

a fastener having a first end portion for engaging a vertebra and a second end portion;

a longitudinal member positionable along the spinal column; and a one-piece connector means for interconnecting said fastener and said longitudinal member, said connector means having clamping means for clamping said longitudinal member to said connector means, and a slot through which said second end portion of said fastener is extendable, said slot having a longitudinal axis extending at an acute angle to the axis of said longitudinal member when said connector means interconnects said longitudinal member and said fastener, said slot enabling adjustment of the distance between the axis of said longitudinal member and the axis of said fastener, a line extending perpendicular to the axis of said fastener and through said clamping means extends at an acute angle to the axis of said longitudinal member when said connector means interconnects said longitudinal member and said fastener.

9. An apparatus as set forth in claim 8 wherein said fastener includes an intermediate portion located between said first and second end portions; said intermediate portion being engageable with said connector means to position said connector means axially along said fastener, said second end portion of said fastener being threadably engageable with a nut; said nut and said intermediate portion of said fastener gripping said connector means to connect said connector means to said fastener.

10. An apparatus as set forth in claim 9 wherein said clamping means includes a set screw engageable with said longitudinal member.

11. An apparatus for retaining vertebrae of a spinal column in a desired spatial relationship comprising:

a fastener having a first end portion for engaging a vertebra and a second end portion;

a longitudinal member positionable along the spinal column; and connector means for interconnecting said fastener and said longitudinal member, said connector means including clamping means for clamping said longitudinal member to said connector means, and means for enabling adjustment of the distance between the axis of said fastener and the axis of said longitudinal member, said means for enabling adjustment including a slot having a longitudinal axis extending at an acute angle to the axis of said longitudinal member when said connector means interconnects said fastener and said longitudinal member, the axis of said fastener being spaced from said clamping means a distance measured along the axis of said longitudinal member when said connector means interconnects said fastener and said longitudinal member.

12. An apparatus as set forth in claim 11 wherein said second end portion of said fastener is extendable through said slot.

13. An apparatus as set forth in claim 12 wherein said fastener includes an intermediate portion located between said first and second end portions; said intermediate portion being engageable with said connector means to position said connector means axially along said fastener.

14. An apparatus for retaining vertebrae of a spinal column in a desired spatial relationship comprising:

a fastener having a first end portion for engaging a vertebra, a second threaded end portion, and an intermediate portion located between said first and second end portions;

a longitudinal member positionable along the spinal column;

a connector member for interconnecting said fastener and said longitudinal member, said connector member including a slot through which said second end portion of said fastener is extendable, said slot enabling adjustment of the distance between the axis of said fastener and the axis of said longitudinal member;

a nut threadably engageable with said second end portion of said fastener to clamp said connector member to said intermediate portion of said fastener; and a set screw threadably engageable with said connector member to clamp said longitudinal member to said connector member;

said slot having a longitudinal axis extending perpendicular to the axis of said fastener, through the axis of said set screw, and at an acute angle to the axis of said longitudinal member when said connector member interconnects said fastener and said longitudinal member, and the axis of said fastener being spaced from the axis of said set screw a distance measured along the axis of said longitudinal member when said connector member interconnects said fastener and said longitudinal member.

* * * * *